US00PP16290P3

(12) United States Plant Patent
Falstad, III

(10) Patent No.: US PP16,290 P3
(45) Date of Patent: Feb. 28, 2006

(54) *HOSTA* PLANT NAMED 'ESKIMO PIE'

(50) Latin Name: *Hosta sieboldiana*
Varietal Denomination: Eskimo Pie

(75) Inventor: Clarence H. Falstad, III, Holland, MI (US)

(73) Assignee: Walters Gardens Inc, Zeeland, RI (US)

( * ) Notice: Subject to any disclaimer, the term of this patent is extended or adjusted under 35 U.S.C. 154(b) by 259 days.

(21) Appl. No.: 10/849,718

(22) Filed: May 20, 2004

(65) Prior Publication Data

US 2005/0262608 P1 Nov. 24, 2005

(51) Int. Cl.
*A01H 5/00* (2006.01)

(52) U.S. Cl. ..... Plt./353

(58) Field of Classification Search ..... Plt./353
See application file for complete search history.

*Primary Examiner*—Anne Marie Grunberg
*Assistant Examiner*—Annette H Para

(57) ABSTRACT

A new and distinct *Hosta* plant named 'Eskimo Pie', characterized by rounded leaves having wide blue-green margins, and a creamy yellow to creamy white center and near white flowers held just above the foliage on thick light green-colored scapes.

2 Drawing Sheets

Botanical classification: *Hosta sieboldiana* (Lodd.) Engl.
Variety denomination: 'Eskimo Pie'.

BACKGROUND OF THE INVENTION

The present invention relates to the new and distinct cultivar of *Hosta*, botanically known as *Hosta sieboldiana* (Lodd.) Engl., and hereinafter referred to as the cultivar 'Eskimo Pie'.

The new plant was discovered by the inventor, Clarence H. Falstad, III, as a non-induced, naturally occurring whole plant mutation of *Hosta* 'Northern Exposure' (not patented) in a plant tissue culture laboratory at a nursery in Zeeland, Mich., USA. Asexual propagation of the plant at the same nursery by tissue culture and division has shown that the unique and distinct characteristics of this new plant are stable and reproduce true to type in successive generations.

*Hosta* 'Northern Exposure' is a sport of *Hosta sieboldiana* 'Elegans' (not patented). 'Elegans' is a large plant with glaucous rugose leaves. *Hosta* 'Northern Exposure' has a wide creamy-colored leaf margin and a blue-green glaucous center. 'Eskimo Pie' has the same cream-colored center as the leaf margin of 'Northern Exposure' and the same blue-green margin as the leaf center of 'Northern Exposure'; a reverse pattern.

The most similar varieties in pattern are 'Dream Weaver' (not patented), 'Great Expectations' (not patented) and 'Thunderbolt' (U.S. Plant Pat. No. 14,232). All three cultivars differ from 'Eskimo Pie' in having leaf centers that are more yellowish-green in the spring, and stay more yellow than 'Eskimo Pie' through the summer under identical growing conditions. 'Dream Weaver', a sport of 'Great Expectations' (which is a sport of 'Elegans'), and 'Thunderbolt', a sport of 'Elegans', appear nearly identical to each other. Both 'Dream Weaver' and 'Thunderbolt' have a much wider margin than either 'Great Expectations' or 'Eskimo Pie', and they retain the same heavier yellowish pigment to the leaf center of 'Great Expectations'.

SUMMARY OF THE INVENTION

*Hosta* 'Eskimo Pie' is unique from its parent sport, *Hosta* 'Northern Exposure' and all other *hosta* cultivars, in several traits. The plant has the following unique characteristics:

1. It emerges yellowish-cream in the leaf centers and lightens to a creamy white in the summer.
2. There are several different intermediate shades of green between the margin and the center as a result of the histogenic layers overlapping each other in uneven patterns.
3. Mature leaves are nearly round, rugose, and have a glucous coating on both sides.
4. The flowers are near-white.

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED BOTANICAL DESCRIPTION

Figure 1:
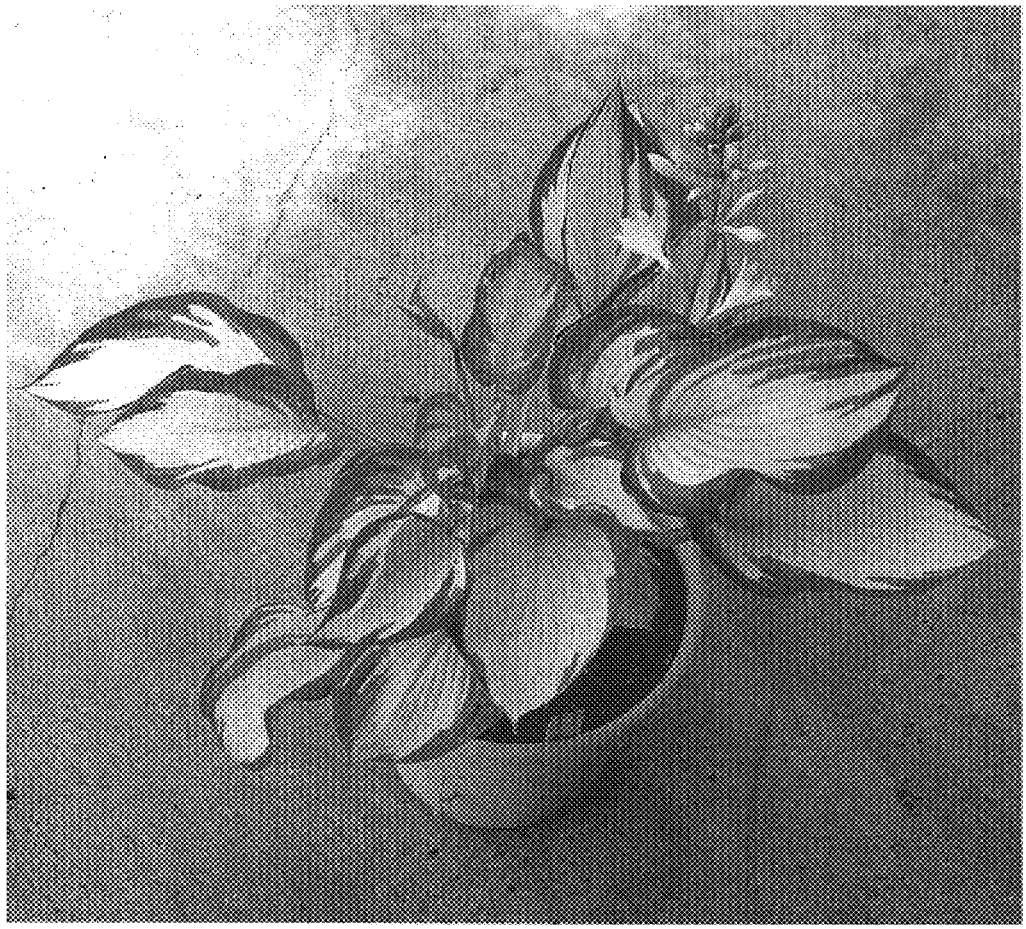
FIG. 1 shows the whole plant.
Figure 2:
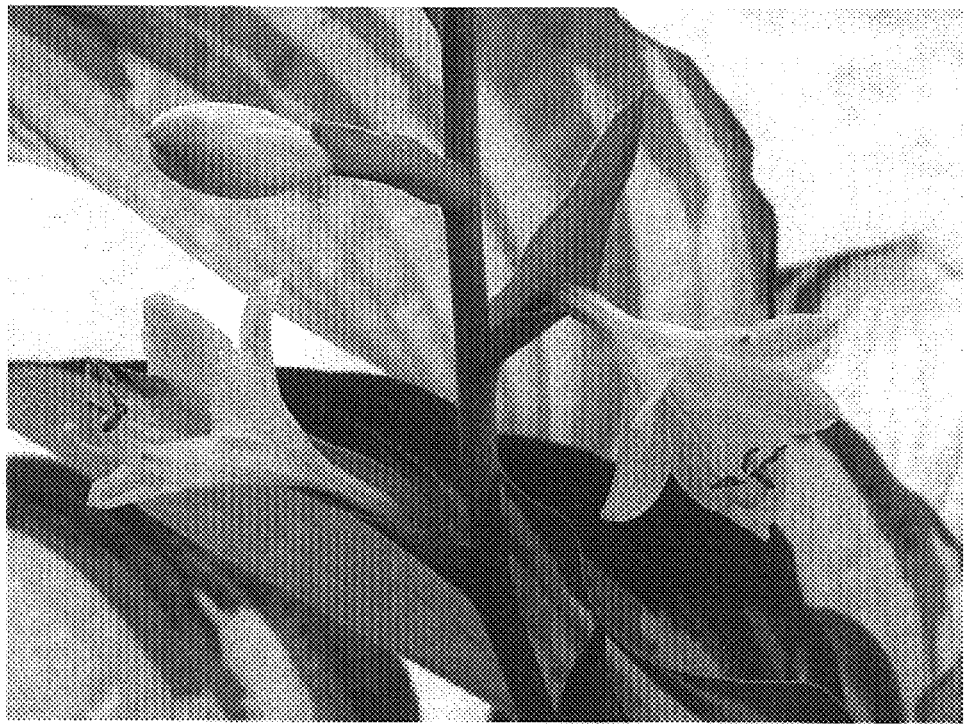
FIG. 2 shows a close-up of the flower and scape.
Figure 3:
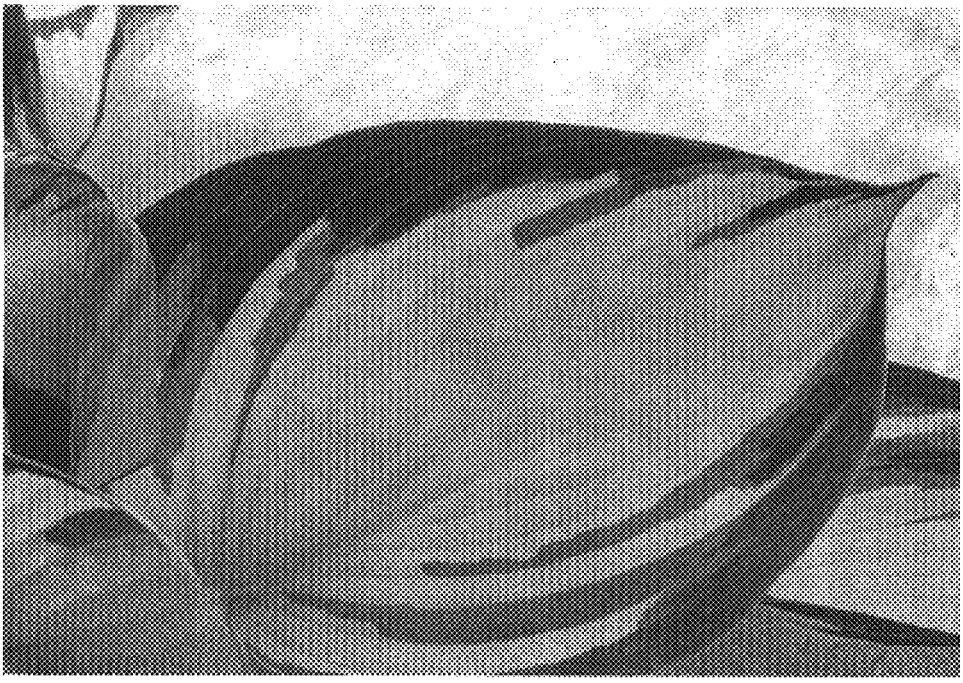
FIG. 3 shows a leaf with the intricate leaf colors.

The following descriptions and color references are based on The Royal Horticultural Society Colour Chart (2001 edition) except where common dictionary terms are used. The new plant, *Hosta* 'Eskimo Pie', has not been observed under all possible environments. The phenotype may vary slightly with different environmental conditions, such as temperature, light, fertility and moisture, but without any change in the genotype. The following observations and size descriptions are of a four-year old plant in a two-gallon container grown in Zeeland, Mich., USA under 50% shade on cloudless days, day temperatures of 18 to 28 degrees C., and night temperatures of 15 to 20 degrees C.

Botanical classification: *Hosta sieboldiana* cultivar 'Eskimo Pie'.

Parentage: Naturally occurring whole plant of *Hosta* 'Northern Exposure' (not patented).

Propagation: Method by tissue culture and division. Time to initiate roots from both division and tissue culture about four weeks from cutting.

Rooting habit: Normal, fleshy, to 3 mm thick, lightly branching.

Plant habit: Herbaceous, densely rhizomatous perennial, symmetrical with radical spreading leaves in an arching mound.

Crop time: Under normal summer greenhouse growing conditions about 26 weeks to finish in a one-liter container. Plant vigor is good.

Plant size: Foliage at flowering is 32 to 40 cm tall and 50 to 60 cm wide.

Foliage description:

Shape and size: Broadly ovate to rounded leaf blades have an acute apex and cordate base. The leaf blades reach 20 to 25 cm long and 18 to 22 cm wide. The leaf blade margin is entire and the green variegation pattern on the edge varies in different regions of the leaf from 10 to 35 mm wide.

Color: Adaxial margin surface emerges RHS 137 B and develops into a deep green closest to RHS 136 A. The inside, or center portion of the leaf is yellow-green, begins nearest RHS 141 D then lightens to yellow RHS 11 C. Abaxial margin surface is RHS 137 B on early young leaves, and RHS 137 A on leaves later in the season. The abaxial leaf center color starts RHS 154 D and lightens to whiter than RHS 4 D with light and heat as the season progresses. There are also three or more intermediate color patterns between the center and the margin. The most prominent adaxial color band is yellow-green RHS 144 A and RHS 138D on the abaxial side. Other more yellow, lighter, or more grayed bands are also sometimes present in thinner and shorter stripes.

Veins: Parallel, deeply furrowed, lighter than RHS 151 D in leaf center of both surfaces; RHS 138 C in leaf margin.

Petioles: 18 to 22 cm long and 6 to 9 mm wide. The center color is RHS 11 C, but varies like the leaves depending on how much light the petiole receives. The edge of the petiole is green RHS 138 C on both surfaces.

Flower description: 30 to 35 per scape, funnelform, 4 to 6 cm wide and 6 to 8 cm long, (distal flowers being smaller), persists for up to two days, scapes remain effective from mid June to early July. No significant floral fragrance has been detected.

Buds: Two to three days prior to opening the buds are lighter than Purple RHS 76D, 6 to 7 cm long, up to 1.5 cm wide.

Tepals: Six, fused at the base, with acute apex, approximately 7 cm long and 1.2 cm wide, arranged in two layers of three, the inner three with clear 1 to 2 mm margin, outer three with tips of green RHS 146 D; base color in center of tepals Red purple RHS 76 D and violet stripes RHS 76 C. The base of the tepals is white.

Peduncle: Erect to 50 cm tall and 0.8 cm in diameter, light green RHS 138 A to RHS 139 A.

Pedicel: Curved, 15 mm long, 3 mm wide, RHS 138 D.

Gynoecium: Style — 5 to 6 cm long, 1 mm diameter, near white, curved upward at distal end; Stigma — white, to 2 mm diameter.

Androecium: Filaments — six, white, approximately 1 mm in diameter and to 5 cm long; Anthers — 5 to 6 mm long, 1.5 mm wide, about RHS 79 A around margin of abaxial side, white in center, pollen is yellow-orange RHS 17 A.

Seeds have not been observed.

Disease resistance: The plant is more resistant to melting-out than most other light-centered varieties, a condition where the light colored leaf center becomes necrotic. It grows best with plenty of moisture and good drainage but is able to tolerate some drought. Hardiness to at least USDA zone 3, and other disease resistance is typical of other *hostas*.

I claim:

1. A new and distinct cultivar of ornamental *Hosta* plant named 'Eskimo Pie' as herein described and illustrated, suitable as a potted plant, for landscaping specimen or in mass, and for fresh-cut arrangements.

* * * * *